(12) United States Patent
Fissan et al.

(10) Patent No.: US 7,812,306 B2
(45) Date of Patent: Oct. 12, 2010

(54) INSTRUMENTS FOR MEASURING NANOPARTICLE EXPOSURE

(75) Inventors: Heinz Fissan, Kerken (DE); Andreas Trampe, Kevelaer (DE); David Y. H. Pui, Plymouth, MN (US); Stanley L. Kaufman, New Brighton, MN (US)

(73) Assignee: TSI, Incorporated, Shoreview, MN (US)

( * ) Notice: Subject to any disclaimer, the term of this patent is extended or adjusted under 35 U.S.C. 154(b) by 431 days.

(21) Appl. No.: 11/439,451

(22) Filed: May 23, 2006

(65) Prior Publication Data

US 2006/0284077 A1    Dec. 21, 2006

Related U.S. Application Data

(60) Provisional application No. 60/683,615, filed on May 23, 2005, provisional application No. 60/763,555, filed on Jan. 31, 2006.

(51) Int. Cl.
*H01J 49/00*    (2006.01)

(52) U.S. Cl. .................. 250/288; 250/281; 250/282; 73/28.01

(58) Field of Classification Search .................. 250/288
See application file for complete search history.

(56) References Cited

U.S. PATENT DOCUMENTS

| | | | |
|---|---|---|---|
| 3,114,877 A | 12/1963 | Dunham | |
| 3,413,545 A * | 11/1968 | Whitby | 324/71.1 |
| 4,312,180 A * | 1/1982 | Reif et al. | 60/39.091 |
| 4,724,394 A * | 2/1988 | Langer et al. | 324/464 |
| 5,026,994 A | 6/1991 | Westcott et al. | |
| 5,352,892 A | 10/1994 | Mordehai et al. | |
| 5,932,795 A * | 8/1999 | Koutrakis et al. | 73/28.01 |
| 5,973,904 A | 10/1999 | Pui et al. | |
| 6,003,389 A | 12/1999 | Flagan et al. | |
| 6,544,484 B1 | 4/2003 | Kaufman et al. | |
| 6,568,245 B2 | 5/2003 | Kaufman | |
| 6,905,029 B2 * | 6/2005 | Flagan | 209/210 |

OTHER PUBLICATIONS

A. Reinert and H. Tammet, Electrical Simulation Of Aerosol Deposition In Lungs, 1995, J. Aerosol Sci., vol. 26, pp. 5613-5614.*

(Continued)

*Primary Examiner*—David A. Vanore
*Assistant Examiner*—Phillip A. Johnston
(74) *Attorney, Agent, or Firm*—Patterson Thuente Christensen Pedersen, P.A.

(57) ABSTRACT

An instrument for non-invasively measuring nanoparticle exposure includes a corona discharge element generating ions to effect unipolar diffusion charging of an aerosol, followed by an ion trap for removing excess ions and a portion of the charged particles with electrical mobilities above a threshold. Downstream, an electrically conductive HEPA filter or other collecting element accumulates the charged particles and provides the resultant current to an electrometer amplifier. The instrument is tunable to alter the electrometer amplifier output toward closer correspondence with a selected function describing particle behavior, e.g. nanoparticle deposition in a selected region of the respiratory system. Tuning entails adjusting voltages applied to one or more of the ion trap, the corona discharge element and the collecting element. Alternatively, tuning involves adjusting the aerosol flow rate, either directly or in comparison to the flow rate of a gas conducting the ions toward merger with the aerosol.

42 Claims, 13 Drawing Sheets

OTHER PUBLICATIONS

A. Reinert and H. Tammet, Electrical Simulation of Aerosol Deposition in Lungs, 1995, J. Aerosol Sci., vol. 26, pp. 5613-5614.*

Fissan et al., "Rationale and principle of an instrument measuring lung deposited nanoparticle surface area," Journal of nanoparticle Research (2006) (7 pages).

Search Report dated, Oct. 13, 2009.

Asbach et al., "Conceptual limitations and extensions of lung-deposited Nanoparticle Surface Area Monitor (NSAM)," Nanoparticles and Occupational Health2008, pp. 101-109.

Brock, "An Instrument for Fast-Response Measurement of Particle Size Distributions in the 4-60 nm Diameter Size Range," Second Joint NSF-ESF Symposium on "Nanoparticles: Technologies and Application" 1999, pp. P15-1-P15-4, Tacoma, Washington, USA.

Chen, "A Nanometer Aerosol Size Analyzer for Rapid Size Distribution Measurements," Second Joint NSF-ESF Symposium on "Nanoparticles: Technologies and Application" 1999, pp. P17-1-P17-2, Tacoma, Washington, USA.

Fissan et al., "Particle Surface Area Concentration Measurement for Smoke Characterization," Institute of Energy and Environmental Technology, 14$^{th}$ Int'l Converence on Automatic Fire Detection AUBE, 2009, Sep. 8-10, 2009, Duisburg Germany.

Fissan et al., "Rationale and principle of an instrument measuring lung deposited nanoparticle surface area," Journal of Nanoparticle Research, 2007, pp. 53-59.

Friedlander et al., "Emerging Issues in Nanoparticle Aerosol Science and Technology," Journal of Nanoparticle Research, 2004, pp. 313-320.

Jung et al., "Response of DC and PAS to size fractionated particles," Dept. of Mechanical Engineering, University of Minnesota, 5$^{th}$ ETH Conference on Nanoparticle Measurement, 2001.

Ku et al., "Comparing Aerosol Surface-area measurements of monodisperse ultrafine silver agglomerates by mobility analysis, transmission electron microscopy and diffusion charging," Journal of Aerosol Science, 2005, pp. 1108-1124, Cincinnati, Ohio, USA.

Li et al., "Evaluation of an electrical aerosol detector (EAD) for the aerosol integral parameter measurement," Journal of Electrostatics, 2009, pp. 1-9.

Medved et al., "A new Corona-Based Charger for Aerosol Particles," Journal of Aerosol Science, 2000, pp. S616-S617.

Qi et al., "The Effect of Particle Pre-Existing Charge on Unipolar Charging and Its Implication on Electrical Aerosol Measurements," Aerosol Science and Technology, 2009, pp. 232-240.

Qi et al., "Experimental study of a new corona-based unipolar aerosol charger," Journal of Aerosol Science, 2007, pp. 775-792.

Reinhart et al., "Electrical Simulation of Aerosol Deposition in Lungs," 1995, pp. S613-S614.

Shin et al., "The effect of dielectric constant of materials on unipolar diffusion charging of nanoparticles," 2009, p. 463-468.

Tsi, "Measuring Nanoparticle Exposure," Application Note NSAM-001, 2008, pp. 1-7.

Tsi, "The Nanoparticle Surface Area Monitor reports the surface area of inhaled particles deposited in the lung" Application Note NSAM-001, 2008.

Tsi, "Model 3070A Electrical Aerosol Detector, a fast aerosol concentration detector for wide dynamic range" 2004.

Tsi, "Model 3550, Nanoparticle Surface Area Monitor, Measures lung-deposited surface area of inhaled particles," 2006.

Tsi, "AeroTrak 9000 Nanoparticle Aerosol Monitor, The AeroTrak 9000 Nanoparticle Aerosol Monitor indicates the surface area of particles deposited in the lung," 2006.

Tsi, "AeroTrak 9000 Nanoparticle Aerosol Monitor Theory of Operation" 2009.

Wilson et al., "Use of Electrical Aerosol Detector as an Indicator for the Total Particle Surface Area Deposited in the Lung," Proceedings of 2004 A&WMA, paper #37, 2004, pp. 1-16.

Wilson et al., "Use of the electrical aerosol detector as an indicator of the surface area of fine particles deposited in the lung," J. Air Waste Manag Assoc., 2007.

Woo et al., "Use of Continuous Measurements of Integral Aerosol Parameters to Estimate Particle Surface Area," Aerosol Science and Technology, 2001, pp. 57-65.

Fissan et al., *Personal Sampler for Measuring the Surface Area of Particles Deposited in the Lung*, Abstracts AAAR, 2003, pp. 280.

Esa, *Corona Charged Aerosol Detection Technology*, www.coronacad.com/CAD_Overview.htm, Nov. 2004, 4 pages.

Fissan et al., *Ecologically Sustainable Nanoparticle Technology*, International Symposium on Environmental Nanotechnology, Dec. 2003, pp. 1-13.

British Associate's response to UK Intellectual Property Office (UKIPO) correspondence, dated Apr. 14, 2010.

British Search Report dated May 26, 2010.

* cited by examiner

INSTRUMENTS FOR MEASURING NANOPARTICLE EXPOSURE

This application claims the benefit of priority of: Provisional Application No. 60/683,615 filed May 23, 2005; and Provisional Application No. 60/763,555 filed Jan. 31, 2006.

BACKGROUND OF THE INVENTION

The present invention relates to systems and devices for measuring concentrations of nanometer or ultrafine particles, and more particularly to such systems that are adjustable in terms of their sensitivities to certain sizes or electrical mobilities of particles or sets of particles within the nanometer range.

When materials are produced or formed in the nanometer size range, i.e. from about 0.1 micrometers in diameter down to molecular levels, they exhibit unique properties that influence their physical, chemical and biological behavior. Nanotechnology, the field of endeavor concerned with materials in this size range, has experienced explosive growth over the last several years as new and diverse uses for nanomaterials are discovered and developed throughout a broad range of industries.

These developments have raised concerns, because the occupational health risks associated with manufacturing and using nanomaterials are not clearly understood. Many nanomaterials are formed from nanoparticles initially produced as aerosols or colloidal suspensions. Workers may be exposed to these particles through inhalation, dermal contact and ingestion, at increased levels due to working environments with nanoparticles in concentrations that far exceed ambient levels. The present invention is concerned with exposure due to inhalation.

Traditionally, health related concerns about airborne particles have focused on particle concentrations in terms of mass per unit volume. Under this approach, permitted maximum concentration standards are determined, and mass concentrations are measured with respect to these standards. However, toxicologic studies involving ultrafine particles (0.1 micron diameter and below) suggest that particle surface area, as compared to either particle number or particle mass, is the better indicator of health effects. This may follow from the fact that for any given shape (e.g. spherical), the smaller the particle, the greater is its surface area compared to its volume or mass. A proportionally larger specific surface area (i.e. surface area divided by mass) increases the tendency of a particle to react with chemicals in the body. Moreover, due to the small mass of nanoparticles, mass concentration measurements are difficult to obtain and lack the requisite sensitivity, even when based on particle accumulation such as through collection of particles on a filter. Particle measurements based on number concentrations are more sensitive, but subject to increased losses and reduced counting efficiency in the nanometer size range. Accordingly, instruments that measure particle concentrations in terms of surface area, especially accumulated or aggregate surface area, are expected to provide more useful assessments of health risks due to nanoparticle exposure.

Another prominent factor influencing the impact of nanoparticle exposure is the region of the respiratory system in which the inhaled nanoparticles are deposited. Deposition in the head (naso-pharyngeal) region raises a risk of particles reaching the brain. In the TB region, cilia tend to remove deposited particles by pushing them toward and into the esophagus. However, particles deposited in the alveolar region are more likely to be transferred to the blood, and less likely to be expelled, because of a less efficient clearing mechanism. The chart of FIG. 1 shows head (H), TB and A region deposition curves (deposition percent vs. particle diameter) over a range of diameters from 1 to 100 nm. The deposition curves are based on the International Commission on Radiological Protection (ICRP) Dosimetry Model, and more particularly were obtained using a computer program known as "LUDEP" available from the UK National Radiological Protection Board. As seen from the curves, alveolar deposition becomes more prominent as particle diameters increase above about six nanometers.

Another factor influencing nanoparticle deposition, and thus health effects, is the level of physical activity. The chart in FIG. 2 plots percent deposition as a function of particle diameter for a variety of activity levels associated with nasal breathing. The curves show deposition in the A and TB regions, over a particle diameter range of about 3.5 to 410 nm, again according to the ICRP Dosimetry Model. In the alveolar region over the ultrafine particle range, higher levels of activity increase the overall deposition percent, and shift deposition toward an increased proportion of smaller particles. In the tracheobronchial region, higher levels of activity reduce the overall deposition percent, but again shift the deposition toward a higher proportion of smaller particles. Finally, deposition varies with the type of individual, based upon such factors as age, sex, size and physical condition.

In FIG. 3, the head, tracheobronchial and alveolar deposition curves from FIG. 1 are weighted to show deposition in terms of surface area concentration, and further are normalized to a sensitivity of 1.0 at a diameter of 100 nm, to show sensitivity as a function of particle diameter. This provides response functions that respectively indicate head, tracheobronchial and alveolar deposition in terms of particle surface area. The chart also shows the geometric surface area ($D_p^2$) function and a number concentration ($D_p^0$) function, both of which appear as straight lines on the log/log scale.

Over most of the 10-100 nm size range, the H, TB and A region response functions are generally linear and have slopes more gradual than that of the $D_p^2$ function. These functions become less linear and diverge toward the $D_p^2$ function as particle diameters decrease. Instruments that employ diffusion charging of aerosol particles, followed by collection of the charged particles to measure the resultant electrical current, tend to correspond more closely to particle diameters than particle surface areas in the particle diameter range of 10-100 nm. However, one such instrument, the electrical aerosol detector (EAD), has been found to exhibit a closer correlation with particle deposition (in terms of particle surface area) based on particle size. This result is confirmed by other instruments (i.e. a scanning mobility particle sizer and an ultrafine condensation particle counter) and a dosimetry model reflecting the tracheobronchial (TB) and alveolar (A) regions. Thus, an electrical aerosol detector or other diffusion charging instrument having a response near the $D_p^2$ function can be used to take measurements over the 10-100 nm size range.

More demanding applications, for example matching mouth and nose breathing at different activity levels, and distinguishing among head region, A region and TB region depositions, require a closer correspondence to actual particle deposition within the lung and elsewhere in the respiratory system. For example, to assess certain health implications, it would be desirable to provide an instrument that more closely simulates the alveolar region as opposed to the tracheobronchial region. One reason, as noted above, is that cilia in the TB region tend to remove deposited particles, while the same particles would tend to remain in the alveolar region.

SUMMARY OF THE INVENTION

The present invention has several aspects, each directed to one or more of the following objects. The first object is to provide a measurement instrument capable of yielding results that correspond more closely to nanoparticle deposition along selected regions of the respiratory system, for example the tracheobronchial region, the alveolar region, or the nasopharyngeal region.

Another object is to provide a particle measuring instrument adapted to be selectively adjustable toward closer correspondence to nanoparticle deposition in different regions of the respiratory system.

A further object is to provide a process for extracting ions and charged particles in a sample aerosol according to a selectable electrical mobility threshold, to more closely simulate a predetermined function describing aerosol particle behavior.

Yet another object is to provide a non-invasive, substantially real time assessment of nanoparticle exposure, in terms of aggregate surface area deposition within one or more regions of the respiratory system.

One aspect of the invention is an aerosol particle sampling instrument. The instrument includes an electrical charging device adapted to bring ions of a gas into a confluence with an aerosol stream including particles, to effect a unipolar charging of the aerosol to produce electrically charged particles. An ion extraction device is disposed along the aerosol stream downstream of the charging device, and is adapted to electrostatically remove excess ions and other higher electrical mobility elements from the aerosol stream. A charge-responsive device is disposed downstream of the ion extraction device, to receive the aerosol stream including electrically charged particles. The charge-responsive device is adapted to generate an electrical signal in proportion to an aggregate charge of the received particles and thereby provide an indication of concentration. The instrument further includes a system tuning component. The tuning component is operable in concert with at least a selected one of the charging device, the ion extraction device, and the charge-responsive device, to adjust an operating parameter of the selected device and thereby selectively alter the indication of particle concentration toward closer correspondence to a predetermined function describing aerosol particle behavior.

The function describing aerosol particle behavior can be a direct numerical concentration function, or may be weighted according to a parameter describing the particles, e.g. particle diameter, surface area, or mass. In connection with weighing the health effects of nanoparticle deposition in the respiratory system, the preferred parameter is particle surface area, due to the increased importance of particle surface area relative to particle mass in the ultrafine size range. Accordingly, while the indication of concentration can be a numerical particle concentration, a particle mass concentration or a concentration based on particle diameters, the preferred concentration indication for assessing respiratory system deposition is particle surface area concentration.

The ion extraction device can include an electrostatic precipitator with an electrically conductive structure, and an electrically conductive element surrounded by and electrically isolated from the conductive structure. Then, the tuning component can comprise a variable voltage source electrically coupled either to the conductive element or the conductive structure. Alternatively, the tuning component comprises a flow control component for varying a flow rate of the aerosol through the ion extraction device.

The preferred charging device comprises an ion generator in the form of an electrically conductive member adapted to provide a corona discharge. Then, the tuning component can comprise a variable voltage source electrically coupled to the conductive member. The charging device further can include a conduit for guiding a carrier gas flow past the ion generator, in which case the tuning component can comprise a flow controller for varying the carrier gas flow rate relative to a flow rate of the aerosol.

The preferred charge-responsive device comprises an electrically conductive filter adapted to entrap the charged particles while allowing air to pass through. An alternative charge-responsive device comprises first and second spaced apart precipitator electrodes. The tuning component comprises a variable voltage source, coupled to the filter or to one of the precipitator electrodes.

Another aspect of the invention is a process for sampling an aerosol to emulate a predetermined function describing aerosol particle behavior, including:

(a) electrically charging particles in an aerosol stream by bringing ions of a gas into a confluence with the aerosol stream;

(b) after charging the particles, extracting ions and other higher electrical mobility elements from the aerosol stream;

(c) after extracting the ions and other elements, generating an electrical signal in proportion to an aggregate charge of the particles present after extraction, thereby providing a concentration indication; and (d) controlling an operating parameter in conjunction with a selected one of generating the ions, extracting the ions, and providing the particle concentration indication, to alter the concentration indication toward closer correspondence to a predetermined function describing aerosol particle behavior.

Preferably the higher electrical mobility elements are extracted using an electrostatic precipitator with a tubular electrically conductive structure that surrounds a conductive element electrically isolated from the structure. Then, the operating parameter can be controlled by adjusting a voltage applied either to the conductive structure or the conductive element. Alternatively, the controlled operating parameter is the dwell time of the aerosol traveling through the electrostatic precipitator. Further alternative operating parameters to control include voltages applied to a corona discharge element that generates the ions, and to an electrically conductive collector used for generating the electrical signal in proportion to the aggregate charge.

A further aspect of the invention includes the combination of a device for selectively modifying a distribution of charged particles in an aerosol stream, and an instrument disposed to receive the aerosol stream from the device and adapted to generate a particle concentration indication based on an aggregate charge produced by the charged particles. The device includes an electrically conductive tubular structure defining a flow passage to accommodate an aerosol stream containing ions and charged particles of a selected electrical polarity. An elongate axially extending electrically conductive element is disposed within the tubular structure and electrically isolated from the tubular structure. A voltage source is electrically coupled to a selected one of the tubular structure and the elongate element to apply a biasing voltage to the selected one. The biasing voltage is of sufficient magnitude to electrostatically remove, from the aerosol stream moving along the flow passage, the ions and the charged particles with electrical mobilities above a given electrical mobility threshold. The voltage source is operable to vary the voltage magnitude and thereby adjust the electrical mobility threshold to selectively modify a distribution of the charged particles in the aerosol stream as it traverses the flow passage, whereby a concentration indication generated by the instrument responsive to receiving the aerosol is altered toward closer correspondence to a predetermined function describing aerosol particle behavior.

According to one preferred approach, the voltage source is operable to provide the biasing voltage at several discrete voltage magnitude levels corresponding to discrete functions describing aerosol particle behavior.

Yet another aspect of the invention is a process for generating a selectively altered aerosol particle concentration indication based on an aggregate charge of a plurality of charged aerosol particles, including:

(a) providing an aerosol stream containing ions and charged particles of a first electrical polarity;

(b) at a first location along the aerosol stream, providing an extraction device;

(c) applying a biasing voltage to the extraction device to remove from the aerosol stream the ions and the charged particles having electrical mobilities above an electrical mobility threshold;

(d) at a second location downstream of the first location, generating an electrical signal in proportion to an aggregate charge of the charged particles present in the aerosol, thereby providing a particle concentration indication altered according to the electrical mobility threshold; and (e) adjusting the biasing voltage to selectively change the electrical mobility threshold.

A further aspect of the present invention is a non-invasive process for assessing nanoparticle exposure in an ambient environment, including:

(a) producing an aerosol stream to sample an ambient environment;

(b) providing, along the aerosol stream: (i) an electrical charging device adapted to bring ions into a confluence with the aerosol stream to effect a unipolar charging of particles in the aerosol stream; (ii) an ion extraction device downstream of the charging device adapted to electrostatically remove excess ions and other higher electrical mobility elements from the aerosol stream; and (iii) a charge-responsive device downstream of the ion extraction device adapted to generate an electrical signal in proportion to an aggregate charge of the particles and thereby provide an indication of concentration;

(c) selecting a nanoparticle deposition function based on a factor selected from the group of factors consisting of: regions within the respiratory system, types of individuals, and levels of physical activity; and (d) adjusting an operating parameter of a selected one of the charging device, the extraction device and the charge-responsive device in accordance with the selected nanoparticle deposition function, thereby to alter the indication of concentration toward closer correspondence with the selected nanoparticle deposition function.

Thus in accordance with the present invention, an aerosol sampling instrument is tunable to produce results that more closely match selected functions representing nanoparticle behavior, e.g. functions describing deposition of nanoparticles in terms of surface area over selected regions of the respiratory system. Tuning is accomplished by adjusting the voltage applied to a selected component of the instrument, such as the ion trap, the corona discharge element or a conductive filter or other charge-responsive device. Alternatively, the flow rate of the aerosol or ion-containing air is adjustable to tune the instrument.

IN THE DRAWINGS

Further features and advantages will become apparent upon consideration of the following detailed description and drawings, in which.

Figure 13:
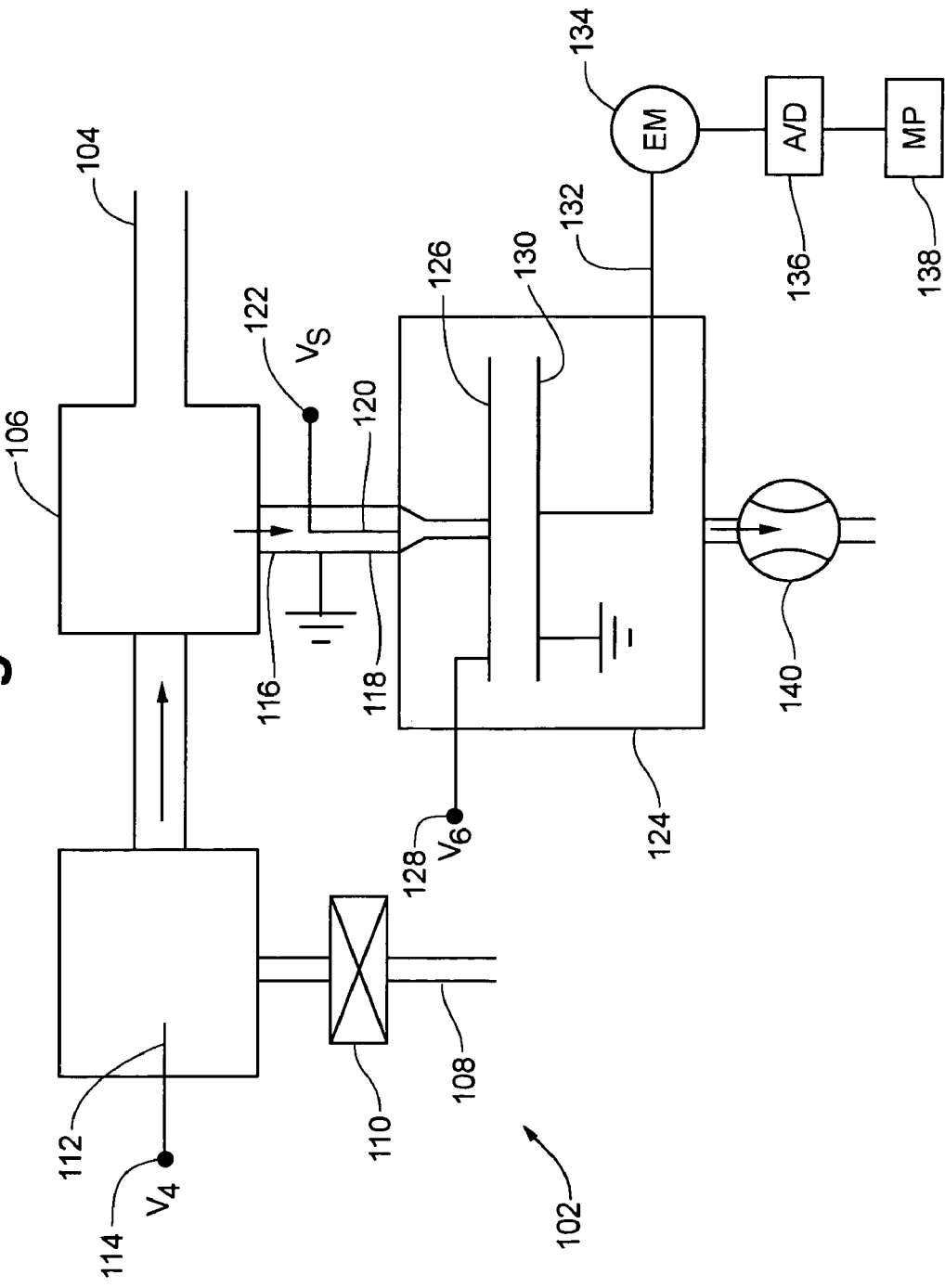
Figure 14:
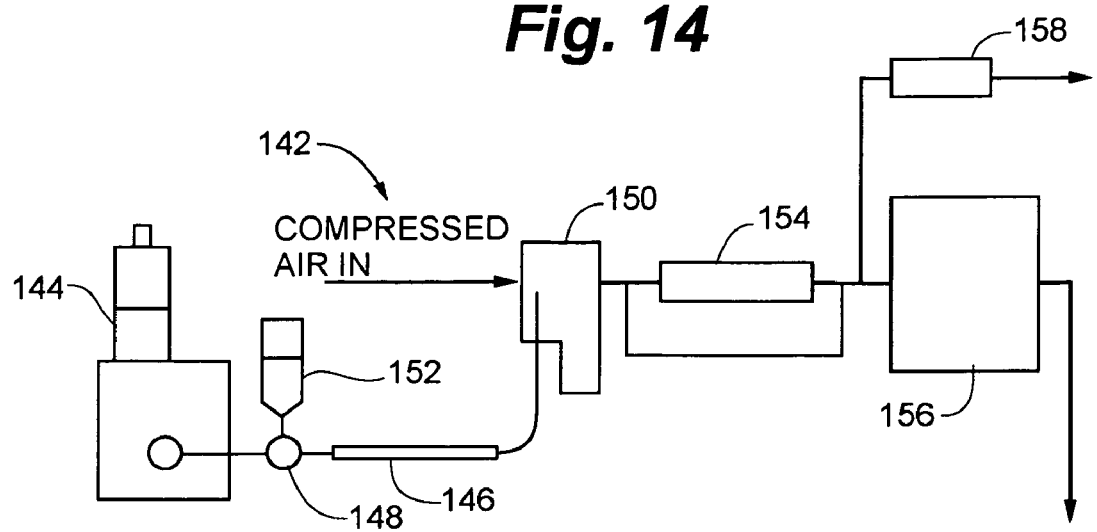
Figure 21:
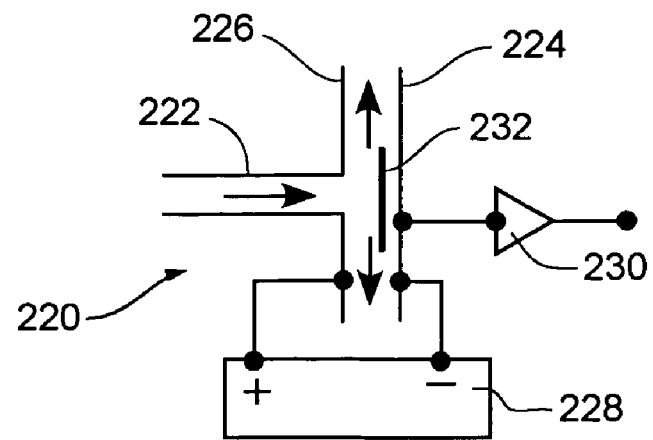

FIGS. 13 and 14 respectively illustrate an alternative embodiment aerosol particle sampling instrument and a particle sampling system;

FIGS. 15-20 illustrate alternative embodiment ion trap configurations;

FIG. 21 illustrates an alternative embodiment charge collecting device; and

Figure 22:
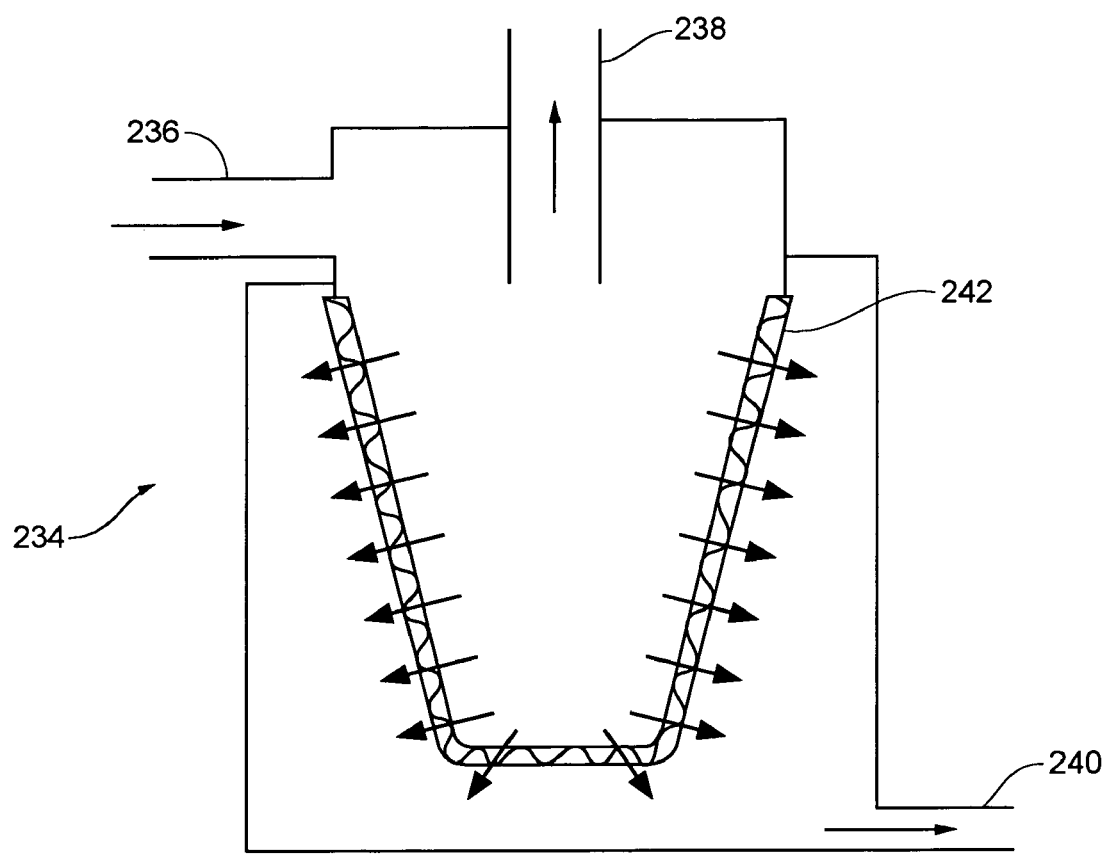
Figure 23:
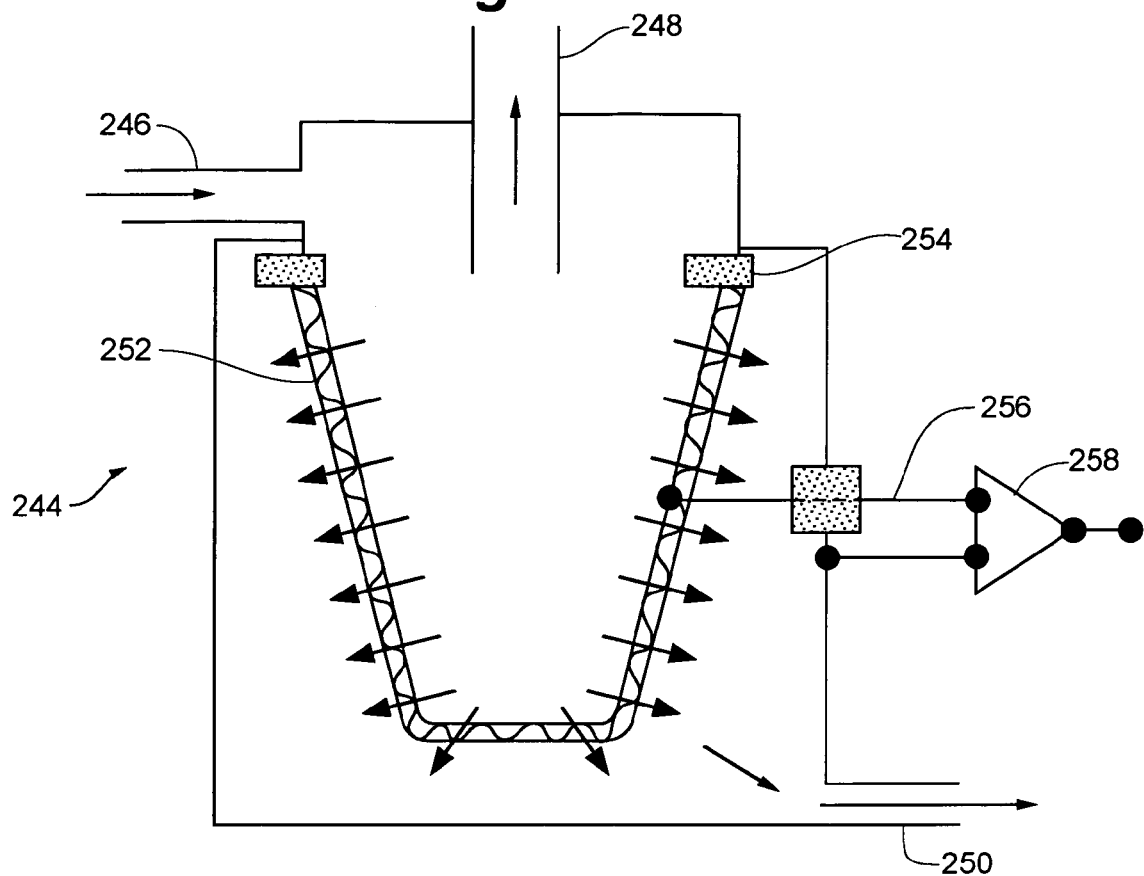
Figure 24:
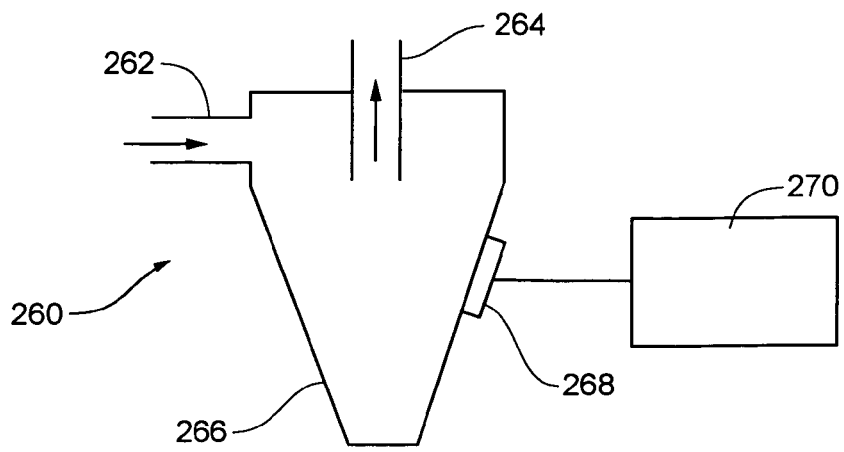

FIGS. 22-24 illustrate large-particle extraction components used in alternative embodiment instruments and systems.

DETAILED DESCRIPTION OF THE PREFERRED EMBODIMENTS

Figure 4:
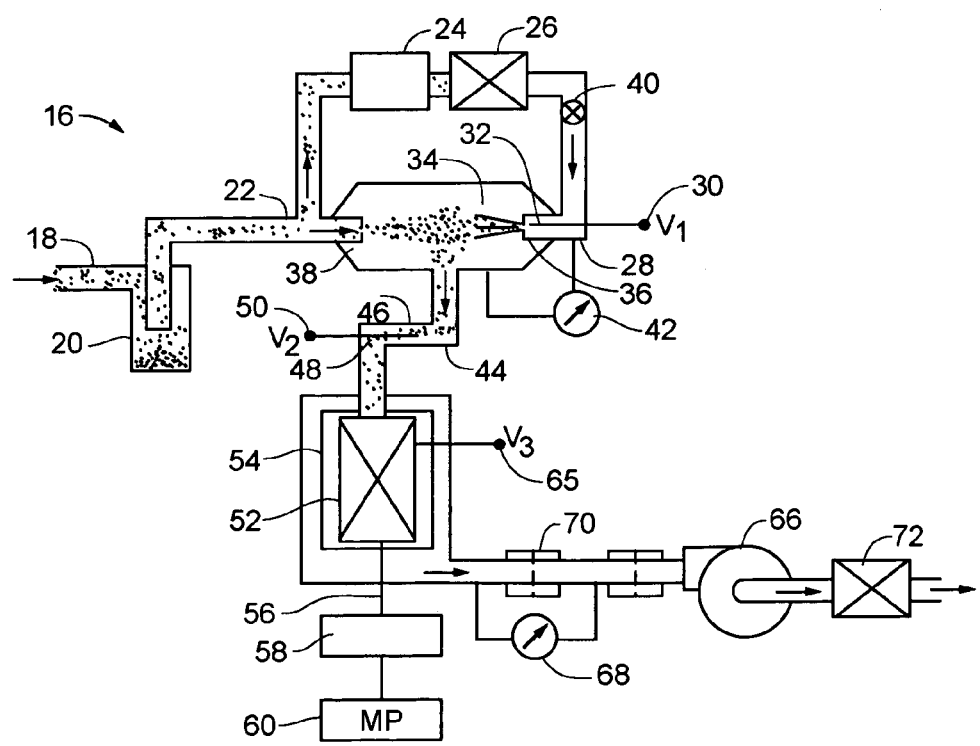
FIG. 4 is a schematic view of an aerosol sampling instrument configured in accordance with the present invention.

Turning now to the drawings, there is shown in FIG. 4 an aerosol particle sampling instrument or device 16. Device 16 is configured to facilitate adjustments to simulate particle deposition in the lung or elsewhere in the respiratory system. An aerosol is received at an inlet conduit 18 and directed through a large-particle separator such as a cyclone 20, to remove particles having aerodynamic diameters that exceed one micron. Flowing at 2.5 lpm, the aerosol reaches a junction 22 where a 1.0 lpm auxiliary flow is diverted through an activated carbon filter 24 and a high efficiency particle air (HEPA) filter 26 to provide a clean air stream. Downstream of filters 24 and 26 is a corona discharge needle 28, which is biased to a high positive voltage e.g. two kilovolts) $V_1$ from a terminal 30. As a result, needle 28 generates positive ions at its tip 32. The clean air stream entrains the ions, conducting them away from tip 32 and into a mixing chamber 34 through an orifice 36.

Meanwhile, the remaining flow of 1.5 lpm is conducted into chamber 34 through an orifice 38 opposite orifice 36, for a turbulent mixture with the positive ions to effect a diffusion charging of the particles suspended in the aerosol. A valve 40 and pressure transducer 42 along the auxiliary flow conduit cooperate to maintain the desired aerosol flow/auxiliary flow ratio of 1.5 to 1.

The aerosol leaving mixing chamber 34 includes a suspension of positively charged particles and positive ions. The aerosol encounters an ion trap 44 including a cylindrical wall 46 maintained at ground, and a coaxial rod 48 biased to a voltage $V_2$ from a terminal 50. The aerosol elements having higher electrical mobilities, primarily the excess positive ions, are repelled away from rod 48, toward and into contact with wall 46, thus to remove them from the aerosol stream. Thus, ion trap 44 functions as an electrostatic precipitator to remove positive ions and positively charged particles having electrical mobilities above a threshold determined by the voltage $V_2$. Voltage $V_2$ can be adjusted to selectively vary the electrical mobility threshold.

Here, "threshold" is used in a qualitative or relative sense, because the extraction of a given particle is influenced by its radial position between the rod and wall, especially if its mobility is near the threshold. Nonetheless, in general, increasing the mobility threshold increases the proportion of elements removed from the aerosol stream.

It is to be appreciated that in the alternative, rod 48 can be biased to a negative voltage to attract the positive ions and charged particles. As a further alternative, wall 46 need not be maintained at ground, but instead can be subject to an applied voltage to increase or decrease the voltage differential relative to the rod.

Figure 5:
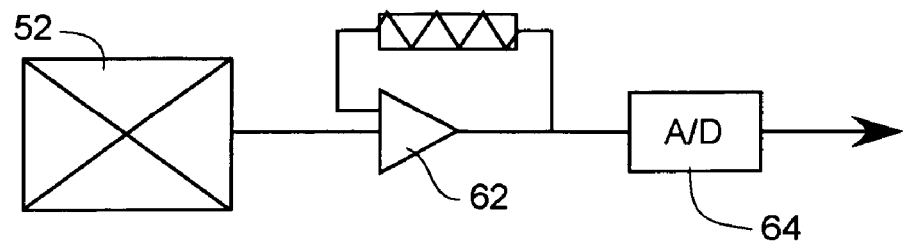
FIG. 5 is a schematic view of electrometer circuitry of the instrument.

From ion trap 44, the aerosol stream proceeds to an electrically conductive HEPA filter 52 that entraps the charged particles. Filter 52, normally maintained at ground, is housed inside a faraday cage 54 which functions as an electrostatic shield. A conductor 56 coupled to filter 52 removes the charge due to the accumulation of particles in the filter. An electrometer measuring circuit 58 generates a signal indicative of the current level in conductor 56, in turn providing a digital input to a microprocessor 60 configured to determine particle concentrations based on the incoming digital signals. More particularly as seen in FIG. 5, the electrometer circuit includes an operational amplifier 62 that generates a voltage level proportional to the current level in conductor 56. The voltage is provided to an analog-to-digital converter 64 which generates the digital input to the microprocessor. Optionally a biasing voltage $V_3$ can be applied to filter 52 from a terminal 65.

A vacuum pump 66, operable in conjunction with a pressure transducer 68 that monitors the pressure difference across an orifice 70, maintains the constant 2.5 lpm total flow as it conducts the aerosol exhaust through a HEPA filter 72.

Figure 6:
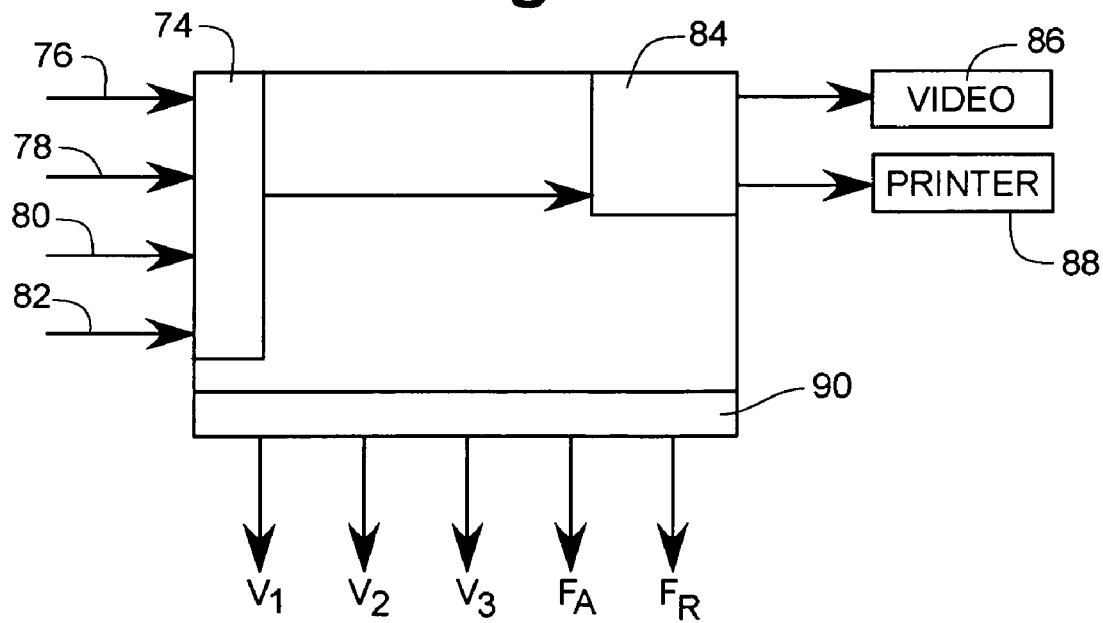
FIG. 6 is a diagram showing a microprocessor of the instrument.

With reference to FIG. 6, microprocessor 60 incorporates internal registers 74 and operating software to receive digital inputs from a variety of sources, including an input from A/D converter 64 representing the electrometer current, inputs 78 and 80 from transducers 42 and 68, and a manual selection input 82 through which system users select an operating mode or particle behavior function to emulate, e.g. alveolar deposition. Internal registers 84 and operating software convert the electrometer current input to functions indicative of surface area concentration, which can be provided to a video terminal 86 or a printer 88 coupled to the microprocessor.

Further internal registers and software, indicated at 90, are operable in response to inputs 76-82 to control the voltage levels $V_1$, $V_2$ and $V_3$ applied respectively to corona discharge needle 28, ion trap 44 and filter 52. Based on input from transducers 42 and 68, software programs 90 maintain the selected aerosol flow rate ($F_A$), and the flow ratio ($F_R$) of the aerosol flow rate to the flow rate of clean air carrying the ions to the mixing chamber. Selection input 82 can be used to select the flow rate and flow ratio.

Sampling device 16 is adjustable to more closely simulate particle deposition in the lung, particularly over the ultrafine particle size range. One approach to achieving this end is to provide an adjustable voltage input to the ion trap, for example at terminal 50 with respect to ion trap 44. The voltage can be adjustable over a wide range, e.g. from 2 to 300 volts. The impact of "tuning" the ion trap in this manner can be understood with reference to FIG. 7, a plot of normalized sensitivity as a function of ion trap biasing voltage, for nine different particle sizes ranging from 10 nm to 100 nm. It is apparent that sensitivity to larger particles remains essentially unaffected by increasing the ion trap voltage, while sensitivity to the smallest particles (10 nm diameter) is reduced generally in proportion to the voltage increase, and is considerably reduced at the highest voltage level. The terms "increase" and "highest" refer to magnitude, since in alternative devices the ion trap voltage can be negative.

It is to be appreciated that if desired, sampling device 16 can be configured to negatively charge the aerosol particles, through application of a negative voltage at terminal 30. In such case, the voltage applied to the ion trap from terminal 50 can be positive to attract ions and charged particles to rod 48, or negative to repel them toward and onto wall 46. As a further alternative, the sampling device may be configured to allow users to select either a positive voltage or a negative voltage to charge the particles.

Figure 7:
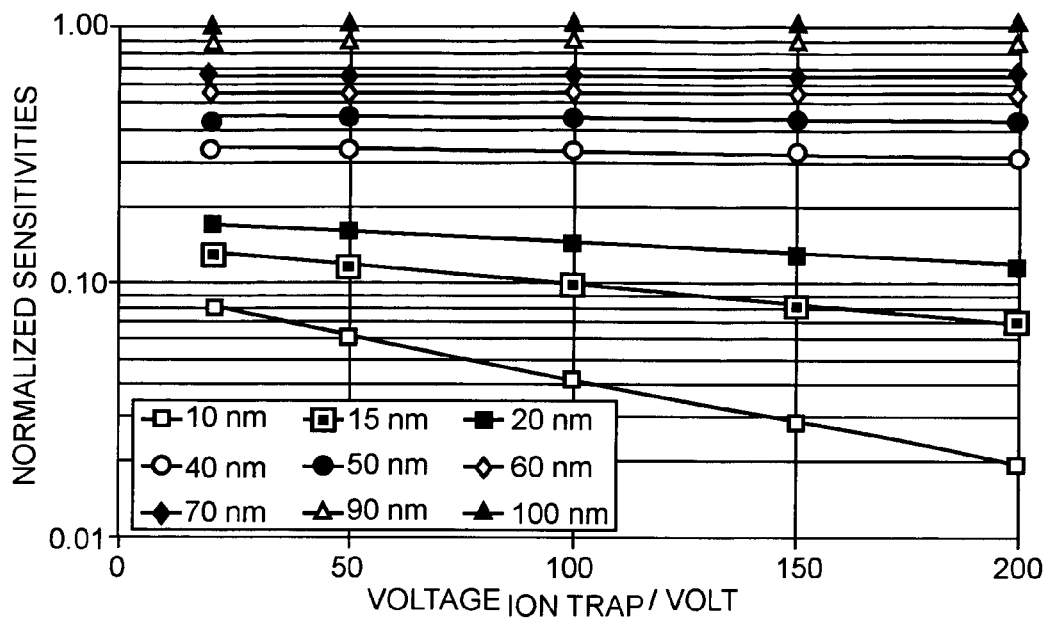
FIG. 7 is a chart showing normalized sensitivities for particles of different diameters over a range of ion trap voltage settings.
Figure 8:
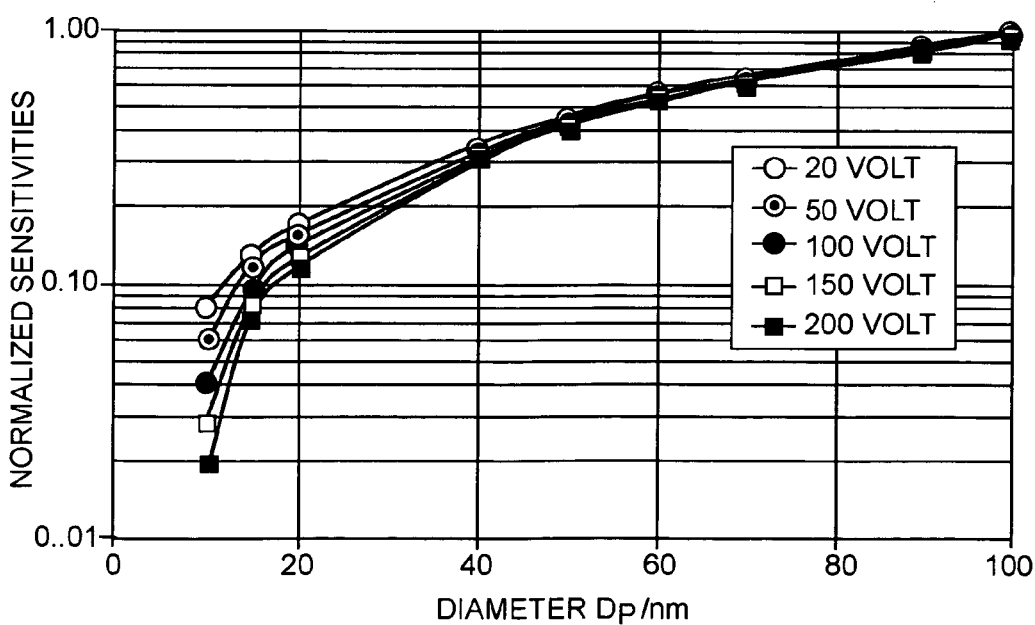
FIG. 8 is a chart of normalized sensitivities for different ion trap voltage settings over a range of particle diameters.

FIG. 8 is a chart showing the data from FIG. 7 as response functions for five different ion trap voltage levels, over a range of particle diameters from 10 nm to 100 nm. The response functions for different voltages begin to diverge from one another at diameters below 40 nm. At higher voltage levels (again in terms of magnitude), an increased proportion of smaller particles is extracted from the aerosol along ion trap 44. Thus, the decreases in normalized sensitivities at smaller diameters are more severe.

Figure 1:
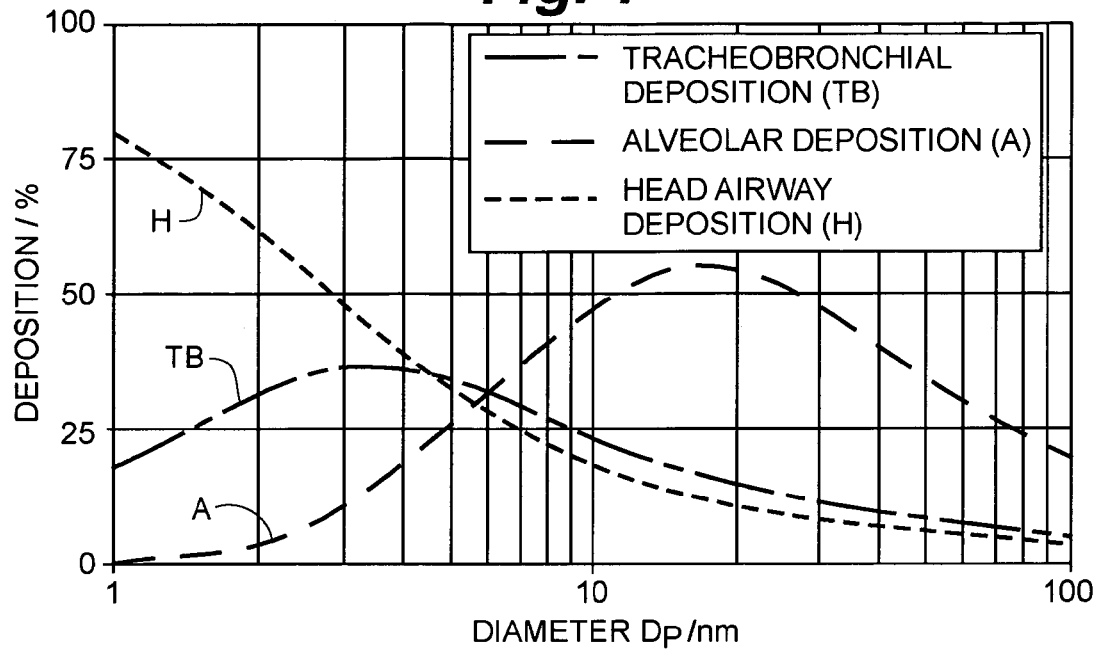
FIG. 1 is a chart showing nanoparticle deposition curves relating to different regions of the respiratory system.
Figure 2:
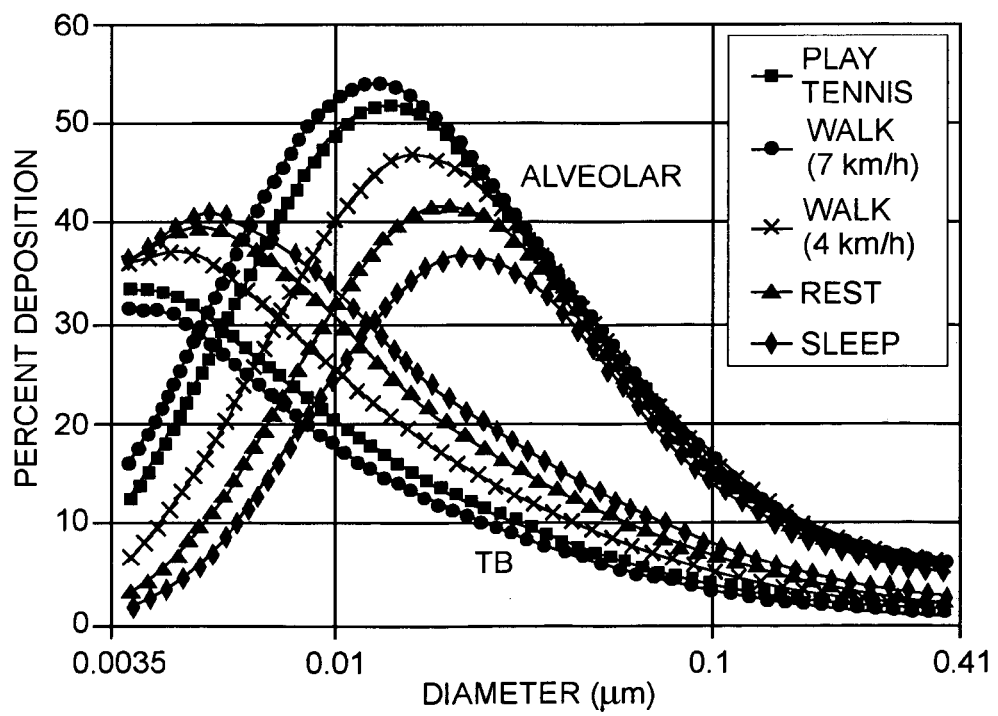
FIG. 2 is a chart showing nanoparticle deposition curves corresponding to different levels of activity.
Figure 3:
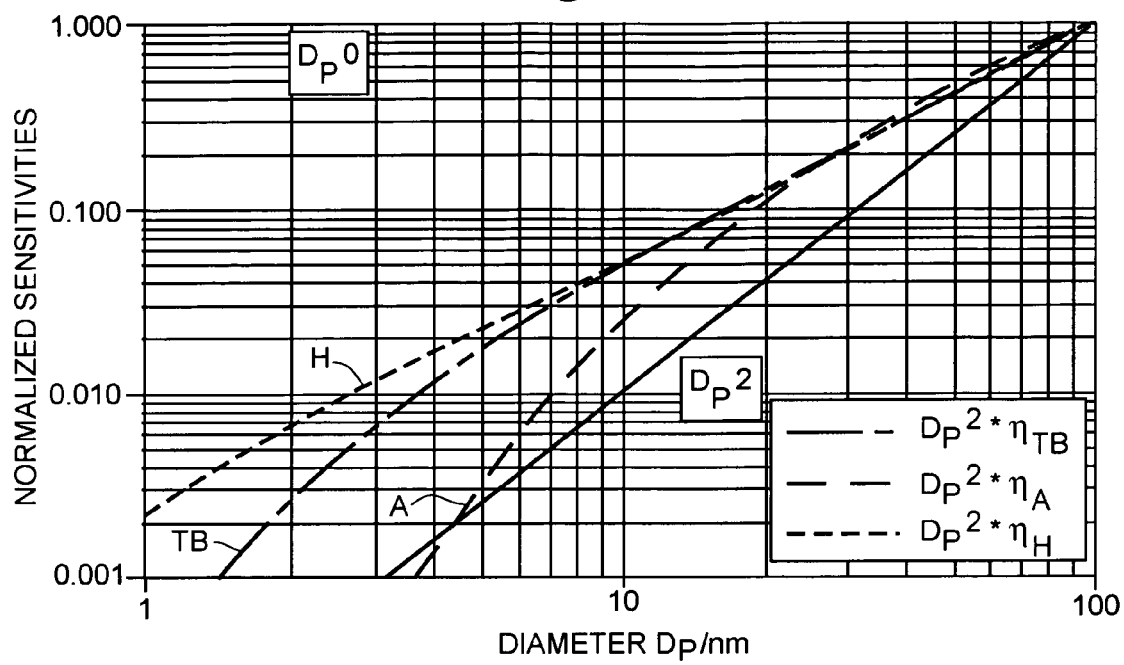
FIG. 3 is a chart showing normalized response functions corresponding to the deposition curves in FIG. 1.
Figure 9:
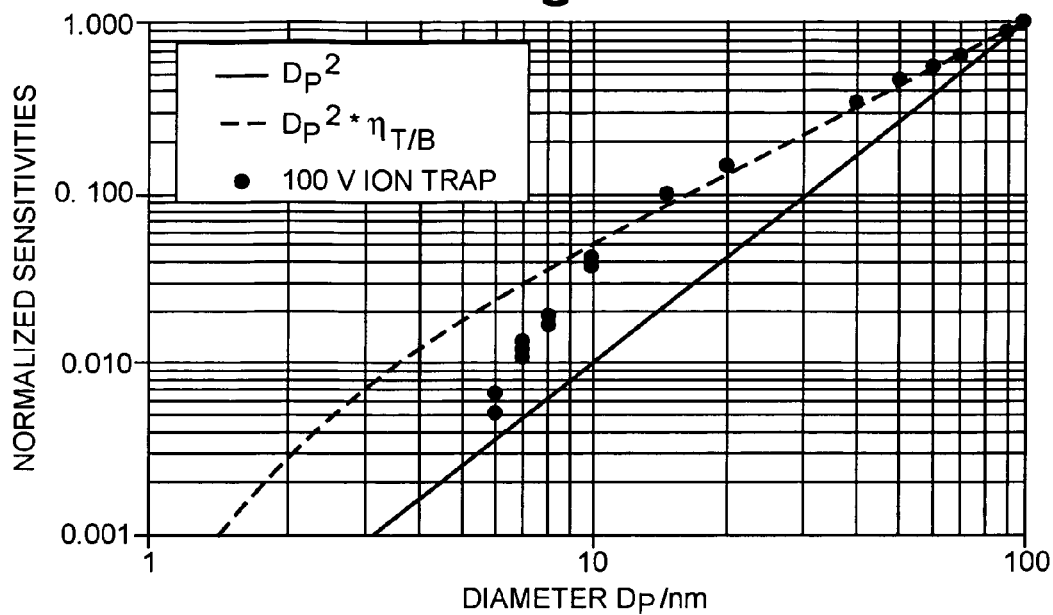
FIGS. 9 and 10 illustrate aerosol particle concentration measurements superimposed on charts of corresponding response functions.
Figure 10:
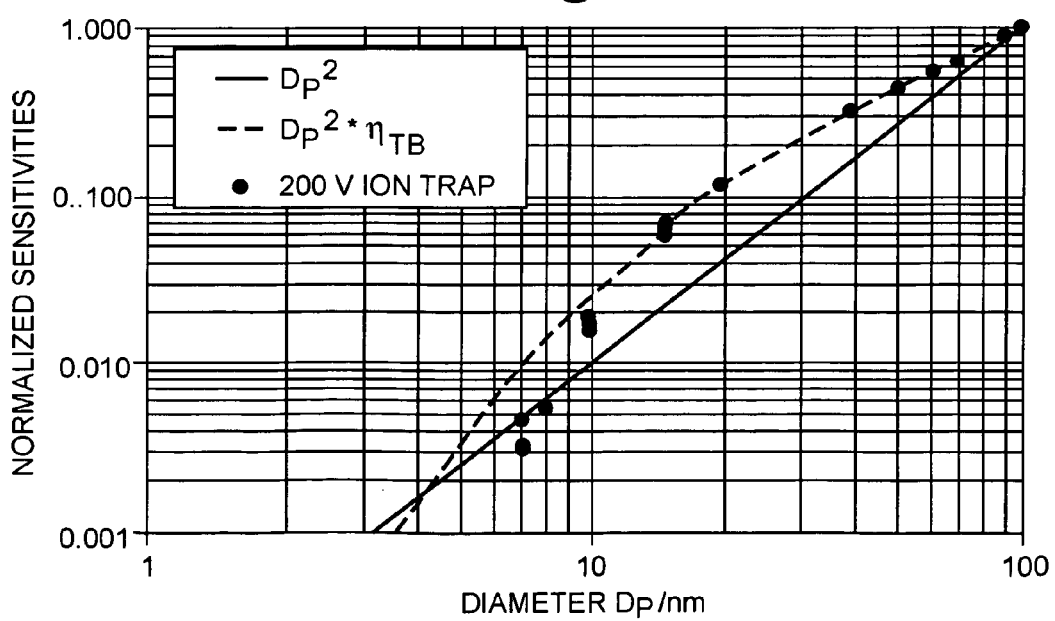

FIGS. 9 and 10 indicate measured response functions as compared to response functions selected from FIG. 3. In particular, FIG. 9 shows the measured response when ion trap 44 is biased to 100 volts as compared to the response function for tracheobronchial deposition, while FIG. 10 compares the measured response when the ion trap is biased to 200 volts as compared to the response function for alveolar deposition. In each case, the measurements match the associated response function over the 10-100 nm range. For sizes below 10 nm, the measurements diverge from the response function in the direction of reduced sensitivity. However, particles having diameters less than 10 nm contribute a minor fraction of the total deposition in the nanoparticle range, particularly in terms of the particle surface area. As a result, the error due to this deviation is negligible.

FIGS. 9 and 10 illustrate how adjustments to the ion trap biasing voltage effectively tune device 16, so that it can more accurately simulate particle deposition in the lung, more particularly in either the tracheobronchial region or the alveolar region.

Figure 11:
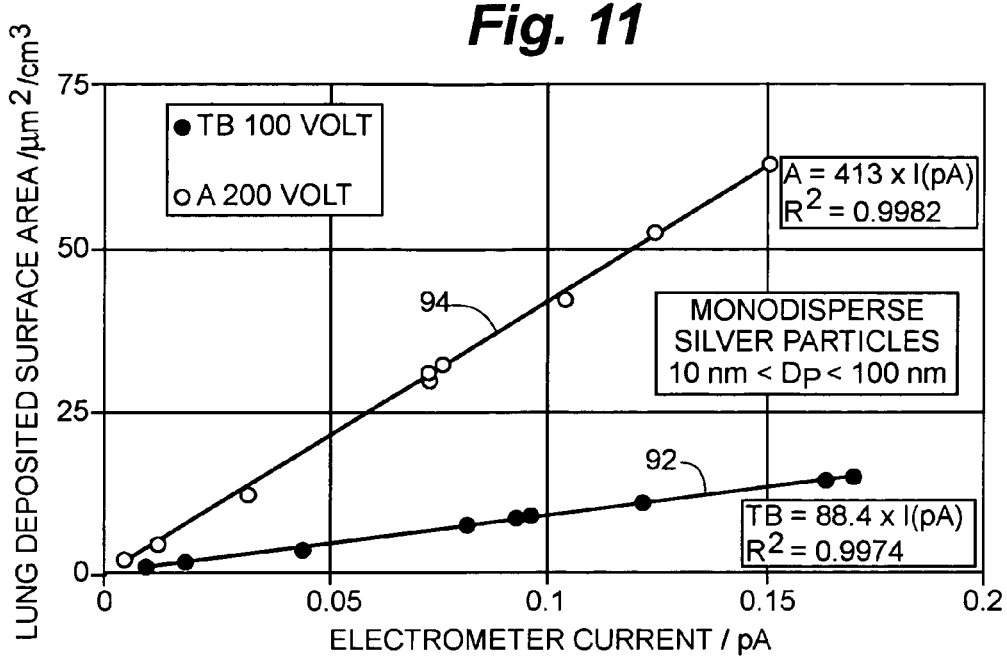
FIG. 11 is a chart illustrating conversion factors relating measured electrical current to surface area concentration.

FIG. 11 is a chart showing nanoparticle deposition in terms of particle surface area as a function of measured electrometer current. An ion trap voltage of 100 volts yields a straight line 92 having a slope of 88.4 in terms of unit surface area deposition (microns squared per cubic centimeter) per unit of electrical current (picoampere). A line 94, corresponding to biasing the ion trap at 200 volts, has a steeper slope of 413. Lines 92 and 94 correspond respectively to tracheobronchial an alveolar region deposition. In each case, the substantially constant slope indicates a simple and reliable relationship between measured electrometer current and particle deposition in terms of cumulative surface area.

Figure 12:
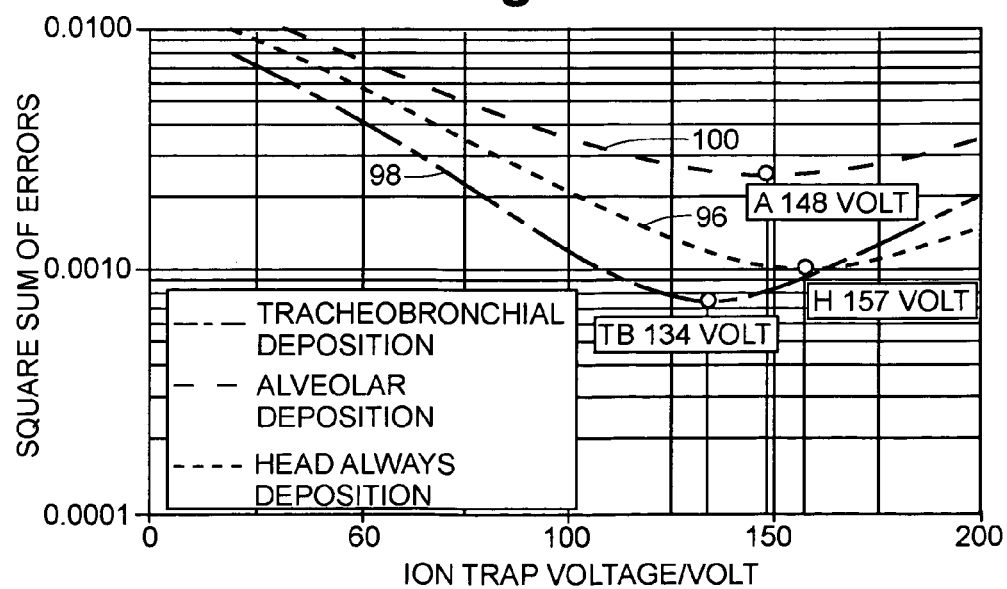
FIG. 12 is a chart illustrating optimum ion trap biasing voltages.

The data depicted in FIGS. 7 and 8 can be used to select optimal ion trap biasing voltages relative to different nanoparticle deposition functions. For example, normalized sensitivities for head, tracheobronchial and alveolar surface-area deposition (as in FIG. 3) can be compared with normalized sensitivities based on measurements corresponding to specific voltage levels (as in FIG. 7) and by interpolating to find normalized sensitivities between the voltages at which measurements are taken. Then, squared differences between the two functions are taken at various voltages. The results with respect to head, tracheobronchial and alveolar deposition are shown respectively by curves 96, 98 and 100 in FIG. 12. In each curve the minimum value, i.e. the point of closest agreement between the calculated and measured functions, yields the optimum ion trap voltage.

As previously indicated, a primary function of the voltage traps in device 16 is to remove excess positive ions from the aerosol stream after it leaves the mixing chamber. The applied voltage produces an electrical field between the rod and the surrounding wall, and as a result, positive ions and positively charged particles are repelled by the rod. It should be noted that alternatively, the ion trap biasing voltage could be negative, with the resulting electrical field attracting the positive ions and charged particles radially inward toward the rod. In either event, the elements removed from the aerosol stream are those having the higher electrical mobilities. These elements are composed primarily of the ions, but also include charged particles having high mobilities, due either to small size or an unusually high level of charge.

When the voltage to the ion trap rod is increased in magnitude, i.e. from 20 volts to 100 volts or to 200 volts as discussed above, the result is a stronger electrical field in the ion trap. Smaller charged particles, with mobilities lower than those of ions but high compared to other charged particles, no longer flow through the ion trap with the aerosol but instead are collected at the rod or surrounding wall, removed from the aerosol. Thus, as suggested in FIGS. 7 and 8, increasing the magnitude of the ion trap biasing voltage primarily affects the smaller charged particles.

It is to be appreciated that tuning device 16 for closer correspondence to particulate surface area deposition in the lung or elsewhere in the respiratory system, does not require a matching of deposition and instrument response with regard to specific particle diameters or ranges of particle diameters. Rather, the object is to match the instrument response to the expected particulate deposition in terms of cumulative or aggregate particle surface area throughout the ultrafine size range. This is consistent with the view, gaining increasing acceptance among toxicology experts, that deposited particulate surface area is the primary factor of interest in determining the health effects of exposure to ultrafine particles.

While adjusting the ion trap biasing voltage is the preferred approach to selectively influencing the makeup of the aerosol leaving the ion trap, an alternative approach is to adjust the aerosol flow rate through the ion trap. Specifically, adjusting pump 66 to reduce the aerosol flow rate increases the "dwell time" of each segment of the aerosol in the ion trap, resulting in increased capture of higher mobility (primarily smaller) charged particles. Thus, reducing the flow rate has generally the same impact as increasing the biasing voltage amplitude.

FIG. 13 schematically illustrates an alternative embodiment aerosol sampling device 102. Device 102 has an inlet conduit 104 for receiving an aerosol and conducting the aerosol to a mixing and charging chamber 106 where particles suspended in the aerosol are positively charged. Another conduit 108 conducts air through a filter 110 and past a corona discharge needle 112 to entrain and carry positive ions to chamber 106. The needle is biased through application of a positive voltage $V_4$ at a terminal 114. The aerosol and ion streams are directed against one another as high velocity jets, to generate turbulence for a more complete mixing and enhanced diffusion charging of the aerosol particles.

Downstream of chamber 106 is an ion trap 116 including a cylindrical wall 118 maintained at ground, and a rod (alternatively a tube) 120 coaxially disposed within wall 118, electrically isolated from the wall and maintained at a relatively low voltage $V_5$ applied from a terminal 122. As the aerosol leaves chamber 106 and flows through ion trap 116, the entrained positively charged particles and positive ions are repelled by rod 120 toward wall 118. The positive ions, having the highest electrical mobility, reach wall 118 and thus are removed from the aerosol stream.

Beyond ion trap 116, the aerosol stream is conducted into a deposition chamber 124 enclosing a pair of spaced apart conductive plates including a plate 126 biased to a high positive voltage $V_6$ from a terminal 128, and a collector plate 130 maintained at ground. A conductor 132 couples collector plate 130 to an electrometer measuring circuit 134. As positively charged particles are collected by collector plate 130, their aggregate charge is drained as a current through conductor 132. Measuring circuit 134 generates a voltage level indicative of the current through conductor 132. The voltage level is provided to an A/D converter 136, which outputs digital values representing the current in conductor 132. The digital output is provided to a microprocessor 138 configured to generate indications of particle concentrations based on the digital values representing current. A vacuum pump 140 draws the aerosol and ion entraining air through the sampling device at a constant rate of 2.0 lpm.

Beyond adjusting the ion trap, devices 16 and 102 may be tuned in other ways to simulate particle deposition in the lung. With further reference to FIGS. 4 and 13, voltage sources 30 and 114 to the respective corona discharge needles can be adjusted to increase or decrease the rate of positive ion production. Alternatively, the flow rates of the aerosol and the ion entraining air into the mixing chamber can be adjusted relative to each other. For example, altering the diversion at the junction to increase the auxiliary flow rate while reducing the aerosol flow rate would reduce the rate at which particles are supplied to mixing chamber 34 or 106 for charging, and the expected result is similar to that due to increasing voltage to the corona discharge needle.

These approaches to tuning would influence primarily the upper region of the ultrafine particle size range, and would tend to increase sensitivity, flattening out the mobility curve. This approach also is subject to particle charge saturation limits.

Yet another approach is to adjust the electrometer stage, e.g. by adjusting the voltage $V_6$ at terminal 128 in sampling device 102, or by applying biasing voltage $V_3$ to normally-grounded filter 52. This approach, like adjusting the degree of particle charging, influences primarily the particles at the upper region of the ultrafine particle size range. A disadvantage of this approach is the potential noise generated at the electrometer stage due to environmental influences such as vibration on the capacitance of the structure.

The invention is applicable to uses other than lung simulation. For example, FIG. 14 illustrates a high performance liquid chromatography separation and measurement system 142. The system employs a high performance liquid chromatography (HPLC) pump 144 and interposes an HPLC column 146 between an injection loop valve 148 and a pneumatic nebulizer 150. The injection loop valve provides substantially instantaneous injections of a liquid sample from a syringe 152 into a stream of water or another carrier liquid. Downstream of the nebulizer is a diffusion dryer 154, which can be bypassed if not needed, in either event ensuring that as the aerosol enters a detector 156, the suspended elements are substantially dry particles rather than droplets. Excess aerosol is vented through a filter 158.

Detector 156 can be substantially similar to either sampling device 16 or aerosol sampling device 102. In either case, detector 156 can be tuned through adjustments to the ion trap, particle charging stage, or electrometer stage as previously explained, so that its output more closely simulates a predetermined function.

Figure 15:
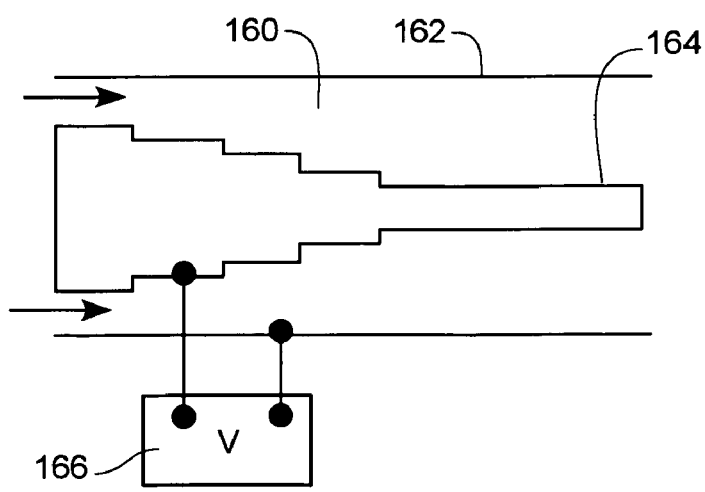

With particular reference to the geometry and electrical biasing of the ion traps, sampling devices 16 and 102 can be modified to produce results that more closely agree with particular lung deposition curves based on the ICRP Dosimetry Model. FIG. 15 illustrates an ion trap 160 including a conductive tubular wall 162 and a conductive ion extraction element 164 disposed coaxially inside the wall. Element 164 has a stepped construction, with sections of progressively smaller diameters in the aerosol flow direction. Given the uniform diameter of the wall, the radial gap between element 164 and wall 162 increases in stepped fashion in the flow direction. A power supply 166 applies a biasing voltage to the extraction element relative to the wall, which can be negative to attract positively charged particles and ions, or positive to repel these particles and ions.

Using average flow velocity, the maximum cutoff length of the ion trap for a given particle size is proportional to the log of the ratio of the wall diameter to the element diameter. The cutoff length also varies inversely with particle mobility. In addition, precipitation along the ion trap is governed primarily by two counteracting factors. First, where the gap between wall 162 and element 164 is narrower, the electrical field is stronger. Consequently, the ions and higher mobility particles move radially more rapidly, either toward element 164 or toward wall 162, for increased precipitation. Further, however, the aerosol flow velocity is higher where the gap is narrower, which tends to reduce precipitation. The axial length of the stepped sections, and reduction in diameter from one stepped section to the next, are advantageously selected with these competing factors in mind.

Figure 16:
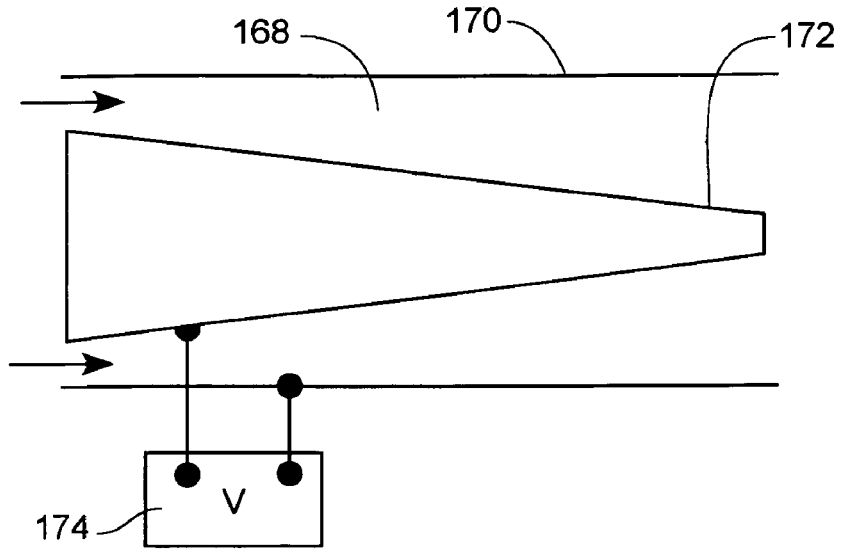

FIG. 16 shows an ion trap 168 with a tubular wall 170 surrounding a conical extraction element 172. A power supply 174 applies a biasing voltage to the extraction element.

The gradual taper of element 172 steadily increases the gap between the element and the wall 170 in the direction of aerosol flow. The same two counteracting factors are present. One advantage of ion trap 168 as compared to ion trap 160, is the smoother aerosol flow, due to the absence of turbulent eddies created by the stepped geometry.

A further modification, not shown, is to reverse the orientation of element 172 to provide a gap radial width that decreases in the aerosol flow direction.

Figure 17:
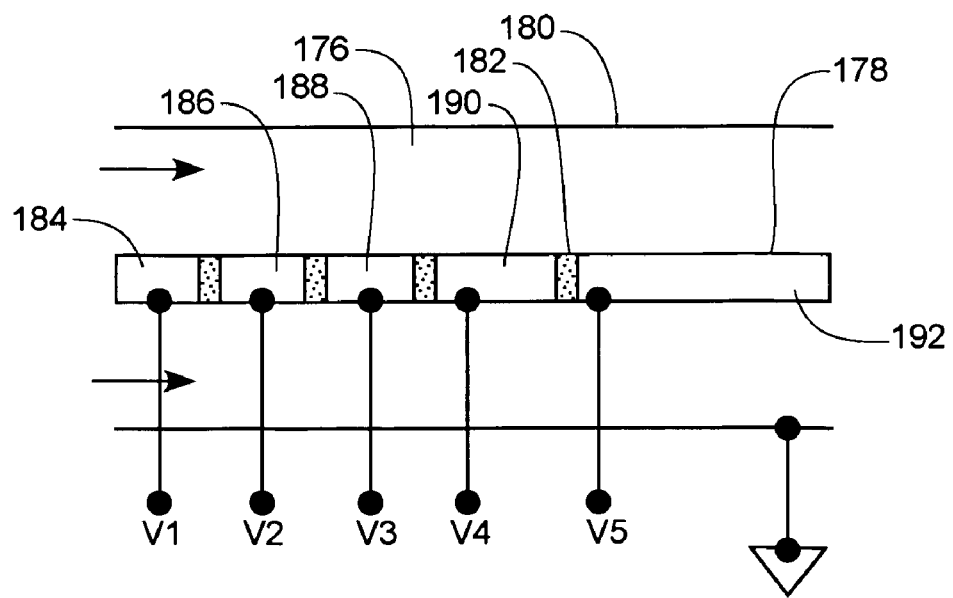

FIG. 17 illustrates an ion trap 176 configured to vary the electrical field in stepped fashion without changing the aerosol flow velocity. A uniform diameter extraction element 178, surrounded by a tubular wall 180, is divided by electrically insulative barriers 182 into a series of conductive, electrically isolated sections 184, 186, 188, 190, and 192, each biased at a different voltage. The length of each section and its biasing voltage are selected in accordance with the principle that the cutoff length for a given segment is inversely proportional to the electric field strength.

Normally all sections are biased to voltages of the same polarity, although one or more sections can be biased at the opposite polarity to steepen the resultant response curve.

Figure 18:
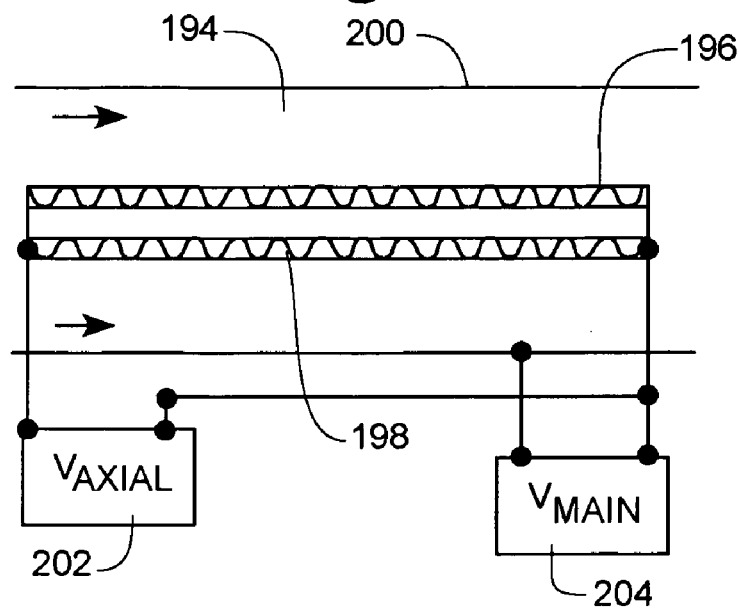

FIG. 18 illustrates an ion trap 194 in which an extraction element 196, covered with a resistive coating 198, is surrounded by a tubular wall 200 and biased at opposite ends by power supplies 202 and 204. This creates a radial electrical field that varies in strength continuously in the axial direction. Coating 198 can be uniform, or varied in thickness to provide another option for tailoring the response function.

Figure 19:
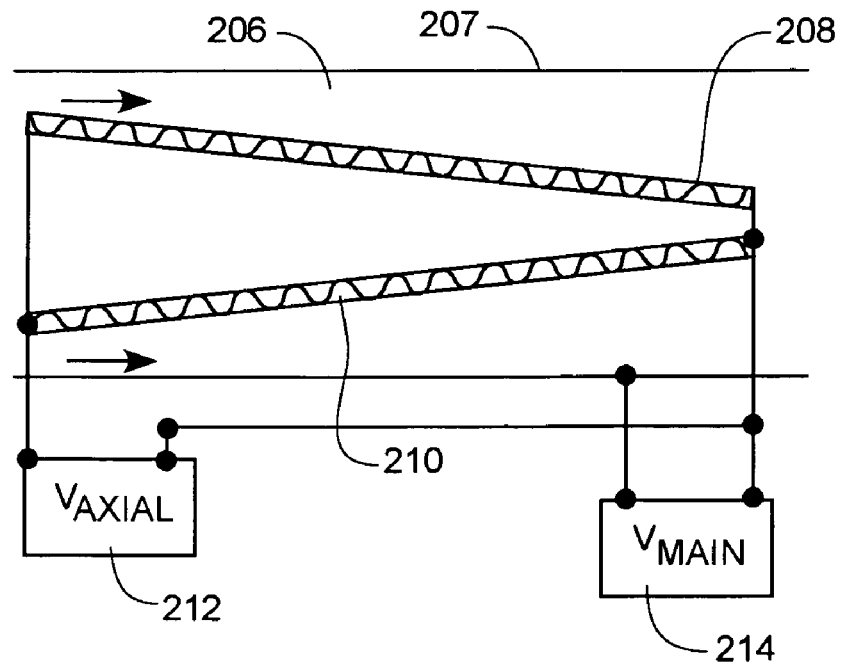

In FIG. 19, an ion trap 206 features a wall 207 surrounding a conical extraction element 208 with a resistive coating 210 biased at its opposite ends with separate power supplies 212 and 214. This design combines the advantages of ion traps 168 and 194.

Figure 20:
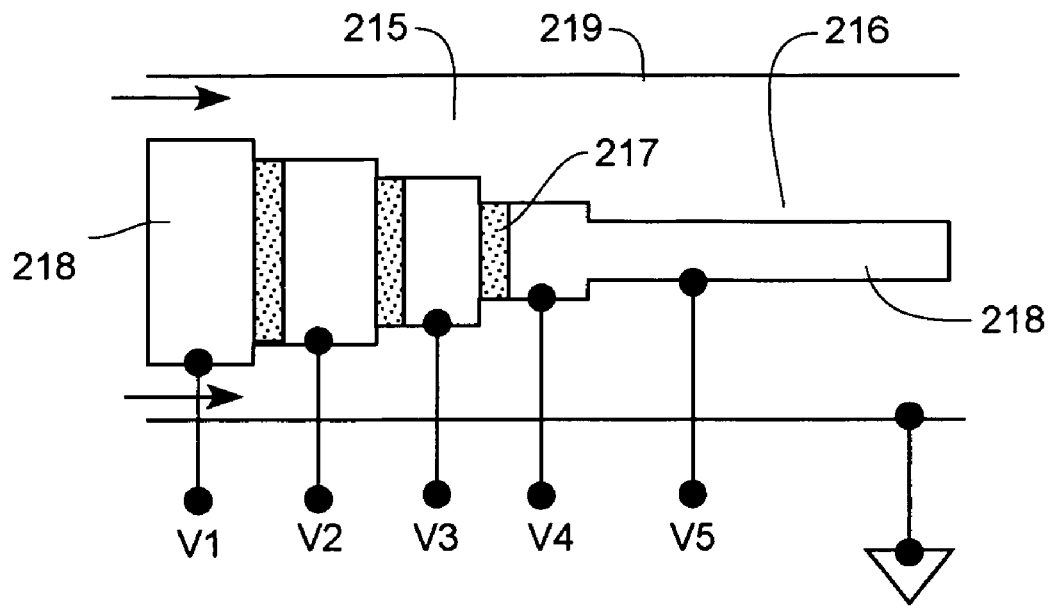

In FIG. 20, an ion trap 215 includes an extraction element 216 of stepped construction and is formed with five electrically isolated conductive segments 218. Segments 218 are individually biased by five independent voltage sources, to provide the combined capability of ion traps 160 and 176. The segments are separated by insulative barriers 217. A wall 219 surrounds element 216.

FIG. 21 illustrates an alternative embodiment charge-responsive device 220 for generating the electrometer output current in lieu of a conductive HEPA filter. The device includes a conduit 222 for channeling the aerosol to a gap between a pair of precipitator electrodes including a collector electrode 224 and a second electrode 226. A power supply 228 biases electrode 226 to a positive voltage and biases the collector electrode to a negative voltage (in the case of positively charged aerosol particles). The collector electrode accumulates the charged particles and provides an electrical current to an electrometer operational amplifier 230, which in turn generates a voltage proportional to the current. This design imposes a cutoff on the large-particle side of the response function. A sample collector 232, mounted to electrode 224, is removable to facilitate microscopic inspection and chemical analysis of collected particles.

As noted above, device 16 includes a cyclone 20 to aerodynamically remove particles larger than one micron in diameter. While this feature is useful, the relatively high transcyclone pressure drop (for example, 80 inches $H_2O$) imposes a high energy requirement, which is particularly disadvantageous for portable, battery-operated sampling instruments.

FIG. 22 illustrates a modified impactor 234 designed for use in lieu of the cyclone impactor. Impactor 234 includes an aerosol inlet conduit 236, an exit conduit 238 for conducting the aerosol to the mixing chamber, and further includes an exhaust conduit 240 to conduct a flow that is metered to ensure a desired rate of flow through conduit 238 to the mixing chamber.

Inside the impactor is a truncated conical porous liner or filter 242 designed to permit passage of air while trapping particles that exceed the cutoff size. The pores in filter 242 are much larger than the cutoff size, e.g. from 10-50 microns in diameter.

An advantage over cyclone impactor 20 is a reduced trans-impactor pressure drop. Further, increasing the metered exhaust flow through conduit 240 can reduce the cutoff size while keeping the pressure drop lower than that of the cyclone. In a preferred version, the cutoff size is 400 nm rather than 1 micron, and the pressure drop across the impactor is considerably less than 80 inches $H_2O$. Another advantage of impactor 234 is that filter 242 can be removably mounted to facilitate inspection and measurement of the large-particle fraction trapped by the filter. This fraction is of interest for its correspondence to the fraction of particles absorbed in the naso-pharyngeal region of the respiratory system.

FIG. 23 illustrates an alternative impactor 244 with an inlet conduit 246, exit conduit 248 to a mixing chamber, and an exhaust conduit 250. An electrically conductive liner or filter 252 is mounted through an insulator 254 to electrically isolate it from the rest of the impactor. A conductor 256 conveys an electrical current from filter 252 to an electrometer amplifier 258.

Filter 252 can provide a real time indication of particle deposition based on the particles collected by filter. Of course, the aerosol is charged before reaching the impactor.

FIG. 24 illustrates a further alternative impactor 260 including an inlet conduit 262 and an exit conduit 264 for conveying the aerosol to a mixing chamber. The impactor employs a solid wall 266 rather than a porous filter. A quartz crystal mass monitor, including a transducing head 268 mounted to the wall and a control and monitoring circuit 270 electrically coupled to the head, provides a continuous indication of particle deposition. The indication is based on a resonant frequency of the crystal, which is reduced by the increase in mass from particle deposition.

Thus in accordance with the present invention, particle sampling instruments are adjustable to provide real time readings that more closely correspond to selected functions describing particle behavior. More particularly in connection with ambient environments, the sampling instruments are tunable to provide non-invasive, real time indications of particulate surface area deposition in selected regions of the respiratory system.

What is claimed is:

1. An aerosol particle sampling instrument, including:
an electrical charging device adapted to bring ions of a gas into a confluence with an aerosol stream including particles, to effect a unipolar charging of the aerosol to produce electrically charged particles;
an ion extraction device disposed along the aerosol stream downstream of the charging device and adapted to electrostatically remove excess ions and to selectively remove other high electrical mobility elements from the aerosol stream;
a charge-responsive device disposed downstream of the ion extraction device, the charge-responsive device being adapted to receive the aerosol stream including the electrically charged particles not removed by the ion extraction device and to provide an indication of particle concentration in proportion to an aggregate charge of the electrically charged particles received by the charge-responsive device; and
a system tuning component operatively coupled with at least one selected device, the selected device being selected from the group consisting of the charging device, the ion extraction device, and the charge-responsive device, the system tuning component being adapted to adjust an operating parameter of the at least one selected device for selective alteration of the indication of particle concentration so that the indication of particle concentration substantially corresponds with that produced by a predetermined nanoparticle deposition function, the nanoparticle deposition function representing a known effect of exposure to nanoparticles.

2. The instrument of claim 1 wherein:
the ion extraction device includes an electrically conductive, electrically biased extraction element.

3. The instrument of claim 1 wherein:
the ion extraction device comprises an electrostatic precipitator including an electrically conductive structure, and an electrically conductive element surrounded by and electrically isolated from the conductive structure; and
the tuning component comprises a variable voltage source electrically coupled to the conductive element and conductive structure to apply a biasing voltage therebetween.

4. The instrument of claim 3 wherein:
the conductive structure is tubular and maintained substantially at ground; and
the conductive element is elongate, coaxial with the conductive structure, and electrically coupled to a variable voltage source adapted to bias the conductive element at a variable voltage with respect to the conductive structure.

5. The instrument of claim 1 wherein:
the tuning component comprises a flow control component for controllably varying a flow rate of the aerosol through the ion extraction device.

6. The instrument of claim 1 wherein:
the electrical charging device is adapted to effect a diffusion charging of the aerosol.

7. The instrument of claim 1 wherein:
the charging device comprises an electrically conductive member adapted to provide a corona discharge, and the tuning component comprises a voltage source electrically coupled to the conductive member and operable to vary the voltage applied to the conductive member.

8. The instrument of claim 7 wherein:
the charging device further includes a conduit for guiding a carrier gas flow past the conductive member to entrain ions and carry the entrained ions into said confluence; and
the tuning component comprises a flow controller for selectively varying a flow rate of the carrier gas with respect to a flow rate of the aerosol.

9. The instrument of claim 1 wherein:
the charge-responsive device comprises an electrically conductive collector adapted to accumulate the charged particles, and a measuring circuit electrically coupled to the collector for measuring an electrical current from the collector.

10. The instrument of claim 9 wherein:
the measuring circuit includes an operational amplifier adapted to generate a voltage level that varies in proportion to the current from the collector.

11. The instrument of claim 10 further including:
an analog-to-digital converter coupled to the amplifier to generate a digital output corresponding to the voltage level, and a microprocessor coupled to receive the digital output of the A/D converter.

12. The instrument of claim 11 wherein:
the microprocessor is programmed to controllably adjust the operating parameter of the selected device in response to receiving a mode selection input from a system operator.

13. The instrument of claim 9 wherein:
the collector comprises an electrically conductive filter adapted to entrap the charged particles while allowing air to pass therethrough, and the tuning component comprises a variable voltage source coupled to the filter.

14. The instrument of claim 1 wherein:
the charge-responsive device comprises first and second spaced apart precipitator electrodes, with a selected one of the electrodes providing a collector adapted to accumulate the charged particles; and the tuning component comprises a variable voltage source coupled to at least one of the electrodes.

15. The instrument of claim 1 further including:

a particle extraction component disposed upstream of the charging device for removing, from the aerosol stream, particles having diameters above a predetermined threshold.

16. The instrument of claim 15 wherein:

the particle extraction component is selected from the group consisting of filters and impaction devices.

17. A process for sampling an aerosol to emulate a predetermined nanoparticle deposition function describing aerosol particle behavior, including:

electrically charging particles in an aerosol stream by bringing ions of a gas into a confluence with the aerosol stream;

after charging the particles, extracting ions and selectively extracting other high electrical mobility elements from the aerosol stream;

after extracting the ions and other elements, generating an electrical signal in proportion to an aggregate charge of the particles present after extraction, thereby providing a concentration indication; and controlling an operating parameter in conjunction with a selected one of said steps of generating the ions, extracting the ions, and providing the concentration indication, to alter the particle concentration indication toward closer correspondence to the predetermined nanoparticle deposition function, the nanoparticle deposition function representing a known effect of exposure to nanoparticles.

18. The process of claim 17 wherein:

extracting the ions comprises using an electrostatic precipitator including an electrically conductive structure surrounding an electrically conductive element electrically isolated from the conductive structure; and controlling the operating parameter comprises adjusting a voltage difference between the conductive structure and the conductive element.

19. The process of claim 17 wherein:

controlling the operating parameter comprises varying a dwell time over which the ions and other higher electrical mobility elements are extracted from any given segment of the aerosol stream.

20. The process of claim 17 wherein:

generating the ions comprises applying a voltage to an electrically conductive member to produce a corona discharge; and controlling the operating parameter comprises setting said voltage.

21. The process of claim 17 wherein:

controlling the operating parameter comprises varying a flow rate of at least one of the aerosol and a gas carrying the ions into the confluence with the aerosol stream relative to the flow rate of the aerosol stream.

22. The process of claim 17 wherein:

receiving the charged particles comprises collecting the particles on an electrically conductive collector, generating the electrical signal comprises measuring an electrical current produced by the collector, and controlling the operating parameter comprises varying a voltage difference between the collector and an electrically conductive structure, the electrically conductive structure being proximate to and electrically isolated from the collector.

23. The process of claim 17 further including:

before charging the particles, removing particles having aerodynamic diameters above a predetermined threshold from the aerosol stream.

24. The combination of a device for selectively modifying a distribution of charged particles in an aerosol stream, and an instrument disposed to receive the aerosol stream from the device and adapted to generate a particle concentration indication based on an aggregate charge produced by the charged particles, wherein the device includes:

an electrically conductive tubular structure defining a flow passage that accommodates an aerosol stream containing ions and charged particles of a selected electrical polarity;

an elongate axially extending electrically conductive element disposed within the tubular structure, the elongate element being electrically isolated from the tubular structure; and a voltage source electrically coupled to the tubular structure and the elongate element to apply a biasing voltage therebetween of sufficient magnitude to electrostatically remove, from the aerosol stream moving along the flow passage, the ions and a portion of the charged particles with electrical mobilities above a given electrical mobility;

wherein the voltage source is operable to set the voltage magnitude to selectively modify the distribution of the charged particles in the aerosol stream as it traverses the flow passage, whereby a concentration indication generated by said instrument responsive to receiving the aerosol is altered toward closer correspondence to a predetermined function, the function being weighted according to a parameter describing the particles.

25. The combination of claim 24 wherein:

the tubular structure is maintained substantially at ground; and the voltage source is electrically coupled to the elongate element.

26. The combination of claim 24 wherein:

the elongate element is mounted coaxially within the tubular wall.

27. The combination of claim 24 wherein:

the voltage source is operable to provide the biasing voltage at a plurality of discrete voltage magnitude levels corresponding respectively to a plurality of discrete functions, each of the plurality of discrete functions being weighted according to the parameter.

28. The combination of claim 27 wherein:

the voltage source is adapted to apply the biasing voltage over a range of from 2 volts to 300 volts.

29. The combination of claim 24 wherein:

the instrument comprises an electrically conductive collector adapted to accumulate the charged particles, and a measuring circuit electrically coupled to the collector for measuring an electrical current from the collector.

30. The combination of claim 29 wherein:

the collector comprises an electrically conductive filter adapted to entrap the charged particles while allowing air to pass therethrough.

31. The combination of claim 29 wherein:

the collector comprises one of a pair of electrodes electrically isolated and spaced apart from one another and maintained at different voltages.

32. The combination of claim 29 wherein:

the measuring circuit includes an operational amplifier adapted to generate a voltage level that varies in proportion to the current from the collector.

33. A process for generating a selectively altered aerosol particle concentration indication based on an aggregate charge of a plurality of charged aerosol particles, including:
- providing an aerosol stream containing ions and a plurality of charged particles of a first electrical polarity;
- at a first location along the aerosol stream, providing an extraction device;
- applying a biasing voltage to the extraction device to remove from the aerosol stream the ions and a first portion of the plurality of charged particles and to allow a second portion of the plurality of charged particles to pass by the extraction device, the aggregate charge of the second portion of the plurality of charged particles substantially representing a predetermined function, the function being weighted according to a parameter describing the particles;
- at a second location downstream of the first location, generating an electrical signal in proportion to the aggregate charge of the second portion of the plurality of charged particles, thereby providing a concentration indication altered according to the second portion of the plurality of charged particles; and
- adjusting the biasing voltage for selective removal of the first portion of charged particles.

34. The process of claim 33 further including:
- selectively varying a radial strength of an electrical field along the extraction device in an axial flow direction.

35. The process of claim 34 wherein:
- the extraction device comprises an electrically conductive extraction element and an electrically conductive tubular wall surrounding the extraction element; and
- selectively varying the strength of the electrical field comprises at least one of: (i) providing the extraction element in a shape selected to vary the radial width of the gap between the extraction element and the tubular wall in the flow direction; and (ii) providing in the extraction element a plurality of electrically conductive sections spaced apart axially and electrically isolated from one another, and electrically biasing the sections at different voltage levels.

36. The aerosol particle sampling instrument of claim 1, wherein the predetermined nanoparticle deposition function describes a particle mass concentration.

37. The aerosol particle sampling instrument of claim 1, wherein the predetermined nanoparticle deposition function describes a particle diameter concentration.

38. The aerosol particle sampling instrument of claim 1, wherein the predetermined nanoparticle deposition function describes a surface area concentration.

39. The combination of claim 24, wherein the predetermined function describes a particle diameter concentration.

40. The combination of claim 24, wherein the predetermined function describes a particle mass concentration.

41. The combination of claim 24, wherein the predetermined function describes a surface area concentration.

42. The aerosol particle sampling instrument of claim 38, wherein the nanoparticle deposition function is representative of the health effects of nanoparticle deposition in the respiratory system.

* * * * *